United States Patent [19]

Rich

[11] 4,032,784
[45] June 28, 1977

[54] METHOD AND APPARATUS FOR EXAMINING A BODY BY A BEAM OF X-RAYS OR OTHER PENETRATING RADIATION

[75] Inventor: Leonard G. Rich, West Hartford, Conn.

[73] Assignee: The Gerber Scientific Instrument Company, South Windsor, Conn.

[22] Filed: Aug. 4, 1975

[21] Appl. No.: 601,308

[52] U.S. Cl. .............................. 250/355; 250/445 T
[51] Int. Cl.² .......................................... G01J 1/42
[58] Field of Search ............... 250/445 T, 354, 355, 250/402, 413, 416

[56] References Cited
UNITED STATES PATENTS 3,906,233  9/1975  Vogel ................................. 250/355
3,924,131  12/1975  Hounsfield ..................... 250/445 T

*Primary Examiner*—Davis L. Willis
*Attorney, Agent, or Firm*—McCormick, Paulding & Huber

[57] ABSTRACT

A system for examining a body through the use of X-rays or other penetrating radiation includes a means or moving a beam of radiation over a body to be examined and a detector for detecting the intensity of the non-absorbed or body-exiting portion of the beam. The system is formed into a dynamic closed loop by comparing the detected beam intensity with a given reference signal and utilizing the error signal so obtained to dynamically vary the body-incident intensity, or body-incident intensity and wavelength, of the beam in such a manner as to hold the detected intensity at a constant value. With the detected intensity held constant, the control signal which dictates the body-incident intensity, or body-incident intensity and wavelength, of the beam becomes a function of the transmissivity of that portion of the body through which the path of the beam instantaneously passes. As the beam is scanned over the body, the beam control signal is supplied to a computer or other utilization device which extracts transmissivity data therefrom and processes such data to compose a pictorial or other graphic display.

19 Claims, 12 Drawing Figures

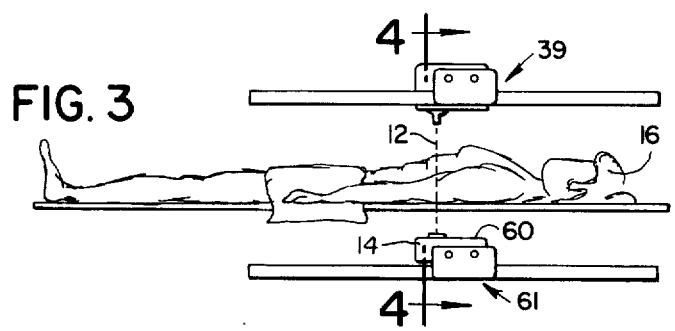
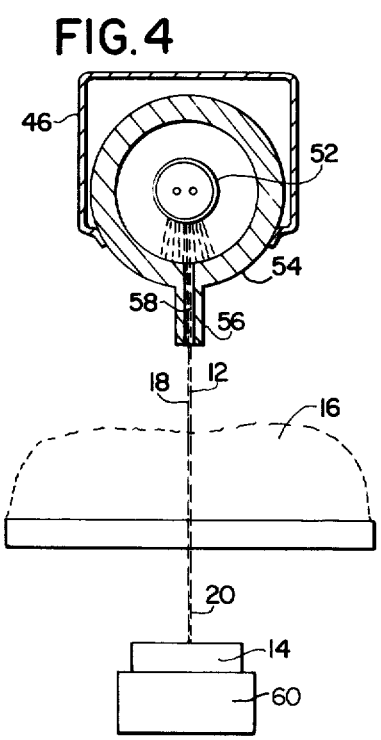
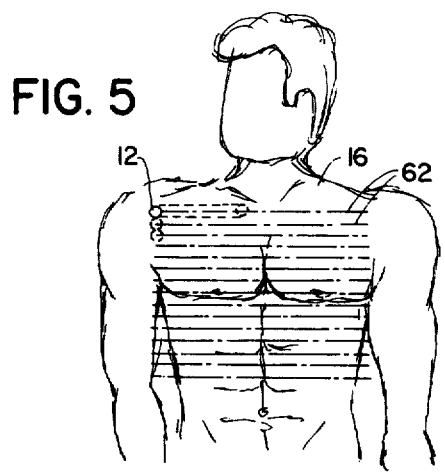
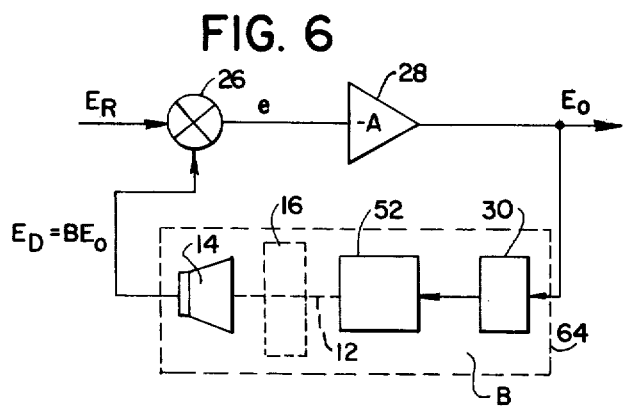

METHOD AND APPARATUS FOR EXAMINING A BODY BY A BEAM OF X-RAYS OR OTHER PENETRATING RADIATION

BACKGROUND OF THE INVENTION

This invention relates to a method and apparatus utilizing X-rays, or other penetrating radiation, to examine a body for the purpose of producing pictures or other graphic displays revealing details of internal body parts, and deals more particularly with such a method and apparatus wherein a body is examined through the use of a narrow beam of rays moved in a scanning motion relative to the body to measure the transmissivity of the body along a large number of straight line paths passing through the body and which transmissivity measurements are then used to compose a point-by-point picture or other graphic display.

A long known and common way of examining a body by means of X-rays is to subject a relatively wide area of the body to a field of X-rays and to expose a photographic film to those rays which rays pass through the body and exit from its other side. Generally, the film used in this procedure has a very high contrast ratio so as to display differences in the X-ray density of a particular tissue, organ, or other object being studied. As a result, information which falls outside the dynamic range of the film is lost. For example, it is almost completely impossible with this method to view both soft tissue and bone in the same X-ray photograph because of their significantly different average densities of X-ray absorption and transmissivity coefficients. Thus, to investigate body parts located in the same portion of the body but having different densities it is normally necessary to take a number of exposures of the same area at different levels of X-ray intensity, thereby undesirably increasing the patient's X-ray dosage.

More recently, various different scanning systems utilizing X-rays have been developed for body examination. These systems usually use a detector whose dynamic range is larger than that of X-ray films and, as a consequence, these systems are generally capable of producing pictures or other displays having much more detail or definition than that provided by photographic films. Often, the improvement provided by such scanning systems is such as to allow body studies to be made without resort to the use of dyes and similar media which are often used to enhance X-ray photographs and which can produce a discomfort and danger to the patient. Also, in a scanning system, the body area examined is investigated point-by-point and the information obtained during the course of a scan may be converted to digital form and computer processed through various techniques, such as some developed by space-photography scientists, to enhance the final image in a number of different ways, as for example, to remove background noise, unwanted features, scanning defects, and the like.

However, regardless of the ability to use computer-enhancement algorithms and techniques to improve the date furnished by X-ray scanning systems, the dynamic limitations of the detectors used in such systems ultimately limit the range and resolutions of the system, as far as its ability to produce good detail and definition over a very wide range of X-ray densities and thicknesses of flesh, bone, organ, tumor, fat and other body material is concerned.

The general object of this invention, therefore, is to provide a system, and related method, for examining a body by X-rays or similar penetrating radiation which system is an improvement on presently known scanning-type systems, particularly insofar as having an extremely wide dynamic range enabling the production of pictures or other graphic displays having high resolution and clear detail. Because of this extremely wide dynamic range the output of the system of the invention is vastly improved in its information content, and therefore enhancement techniques are much more effective and allow a better application of enhancement algorithms.

Another important object of this invention is to provide an apparatus and method of the foregoing character wherein the radiation dose received by the patient during the examination may be held to an absolute minimum. In particular, the system operates to hold constant the intensity of the radiation detected by the detector by varying the emitted or body-incident radiation. Since the detector can operate at a very low level of detected intensity, body-incident radiation need only be sufficient to maintain such low detected level. Also, since the useful range of the system is very great, the information derived from a single scan may be processed to produce a number of different pictures each viewing body parts having different X-ray densities. That is, computer programs associated with this system will allow any density range to be examined and enhanced or rejected in the resulting picture or display.

In the system of the invention a body-incident beam of radiation is dynamically varied, either in intensity or in both intensity and wavelength as the beam, because of its scanning motion, encounters regions of differing transmissivity or X-ray density to keep the body-exiting radiation at a constant intensity. Basically, as the transmissivity of the beam path through the body decreases the intensity of the body-incident beam is increased. The body-incident beam intensity is the only factor varied in accordance with one embodiment of the invention. In accordance with another embodiment of the invention, the mean wavelength of the beam is varied along with the body-incident beam intensity and in such a manner that the wavelength is shortened as the intensity is increased. That is, softer X-rays are used when going through softer or less X-ray dense tissue and harder X-rays are used when going through harder or more X-ray dense tissue. This can be used to advantage in some cases to bring out still more detail in the resulting picture or other display.

Other objects and advantages of the invention will be apparent from the following description and from the drawings forming apart hereof.

SUMMARY OF THE INVENTION

This invention relates to a method and apparatus for examining a body through the use of a beam of X-rays or other penetrating radiation wherein the beam is moved in a scanning motion relative to the body and its body-incident intensity, or body-incident intensity and wavelength, is controlled through a dynamic feedback loop to maintain the intensity of the body-exiting radiation, as detected by an associated detector, at a constant value. The instantaneous value of the control signal which controls the emitted beam intensity, or the emitted beam intensity and its wavelength, is thus a function of the transmissivity of the instantaneous beam path through the body, and such control signal, or other signal representative thereof, is supplied to a computer or other utilization device to provide information about the transmissivity of the body along a large number of straight line paths for use in composing a picture or other display revealing internal features of the body.

The invention more particularly resides in a method and system wherein a ray generator, collimator and scanner move a beam of X-rays in a scanning manner across a body area to be studied. A detector on the other side of the body detects the intensity of the radiation passing through and exiting from the body. This detected intensity is compared with a reference signal and an error signal so produced is used to control the X-ray generator to vary the intensity, or intensity and wavelength, of its emitted beam in such direction as to reduce the error signal and thereby maintain the detected body-exiting intensity at the level set by the reference signal. The open loop gain A and the feedback coefficient B are of such signs and values that the feedback is negative and the absolute value of the feedback factor $|AB|$ is very much greater than one, thereby causing the body-incident intensity to accurately represent a linear or other desired function of the feedback coefficient which in turn is a function of the measured transmissivity.

The invention also resides in using, in the feedback circuit of the system, a nonlinear amplifier or network to compensate for nonlinearities otherwise existing in the transfer function between the system output signal and the measured transmissivity to cause the output signal to be related to the transmissivity by a linear, logarithmic or other desired function.

BRIEF DESCRIPTION OF THE DRAWINGS

FIG. 3 is a side view of FIG. 2, this view also showing the detector and an associated positioning mechanism.

FIG. 4 is a simplified vertical sectional view taken through the X-ray generator and collimator of FIG. 2 generally on the line 4—4 of FIG. 2.

FIG. 5 is a view showing a representative scan path for the beam of the system of FIG. 1.

FIG. 6 is a schematic view generally similar to FIG. 1 but showing the parts thereof arranged to illustrate better the closed loop nature of the system.

FIG. 7 is a view similar to FIG. 6 but illustrates an alternative embodiment of the invention wherein a nonlinear network is included in the feedback circuit to provide a linear or other desired shape to the characteristic curve of the output signal.

DETAILED DESCRIPTION OF THE PREFERRED EMBODIMENTS

Figure 1:
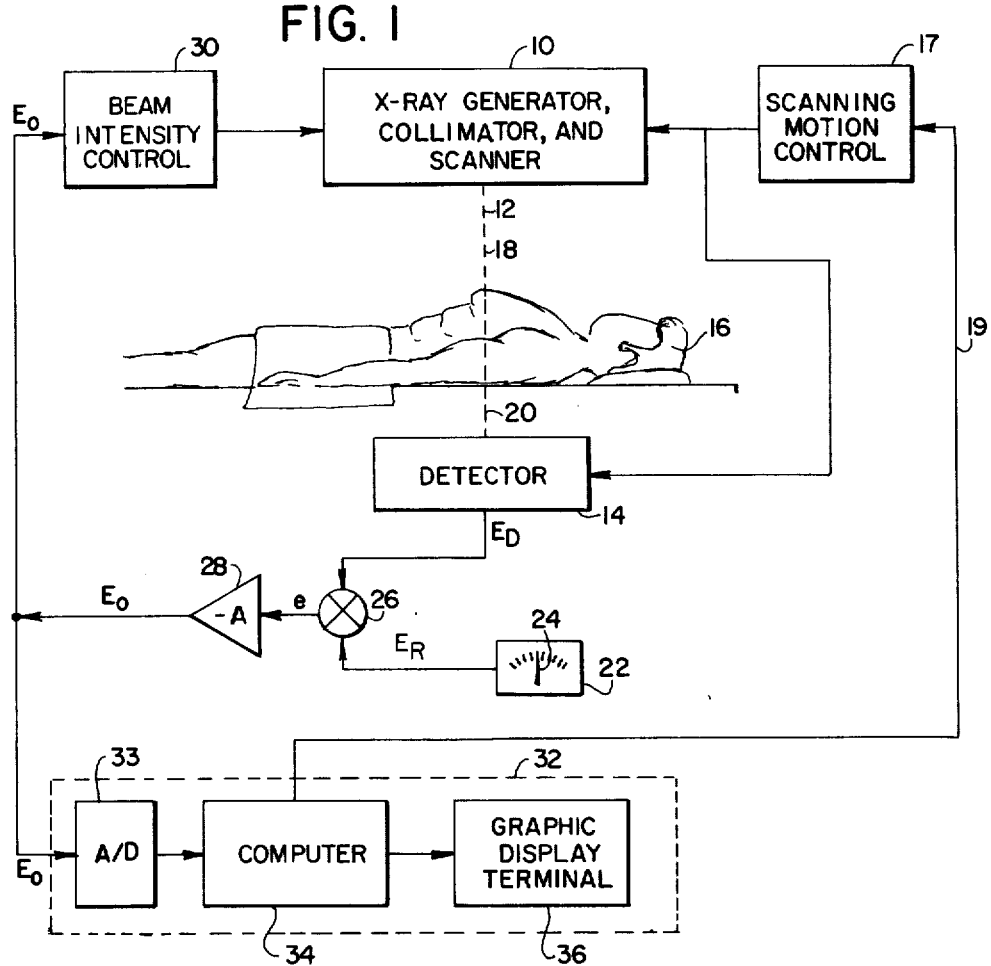
FIG. 1 is a schematic diagram of an X-ray scanning system embodying the present invention.

Referring first to FIG. 1, a system embodying this invention is there shown and includes a means 10, consisting of an X-ray generator, collimator and scanner, for producing a collimated beam 12 of X-rays directed toward a related detector 14. The space between the mechanism 10 and the detector 14 is an examining space into which a body 16 or body part may be placed so as to be intercepted by the beam. The detector 14 converts the detected radiation intensity to a related detected intensity voltage signal $E_D$. The detector may take various different forms without departing from the invention and, by way of example, may consist of a short persistence fluorescent screen and a photomultiplier tube viewing the entire screen. Hereinafter the detector 14 is described as a small area unit which is moved in unison with the scanning movement of the beam 12, but this is also not essential and it could instead be a fixed unit with a sufficiently large sensing area as to intercept the beam throughout all of its scanning movement.

FIG. 1 also illustrates two different portions of the beam 12. The first is an emitted or body-incident portion 18 which is emitted from the mechanism 10 and which strikes the body 16. The second is a body-exiting portion 20 which passes from the body to the detector. As the beam 12 passes through the body, a part of it is absorbed by the parts of the body which it encounters, and different body parts have different absorption or transmissivity coefficients. Thus, the difference between the intensity of the body-incident portion 18 of the beam 12 and that of the body-exiting portion 20 is a measure of the total absorbtivity or transmissivity of the instantaneous beam path through the body. The scanning movement of the beam 12 is controlled by a scanning motion control unit 17 which responds to information from a computer 34 supplied on the line 19.

The detected intensity signal $E_D$ is compared with a reference signal $E_R$ supplied by a reference signal source 22 preferably having a manually movable member 24 by means of which the reference signal $E_R$ may be set to any desired value. The comparing means comprises a summing circuit 26 which sums the two signals $E_D$ and $E_R$ to provide an error signal $e$ supplied to an amplifier 28. The amplifier 28 is an operational amplifier having a high gain A. The detected intensity signal $E_D$, and the reference signal $E_R$ are of opposite signs so that in the summing circuit 26 these two signals are actually subtracted to produce the error signal $e$. For the purpose of explanation, the summing circuit 26 and amplifier 28 have been shown separate from one another, but it will be understood that, if desired, the functions of these two components may be conveniently served by a single differential operational amplifier having as inputs thereto the two signals $E_D$ and $E_R$.

The output of the amplifier 28 is an output voltage signal $E_O$ which is supplied, as a control signal, to a beam intensity control device 30 which, in response to changes in the output $E_O$, effects corresponding changes in the X-ray generator to vary the emitted or body-incident intensity of the beam 12. The signal $E_O$ is also used as a transmissivity information containing signal which is supplied to a utilization device 32. The nature of the utilization device may vary widely, but in the present case, it is shown, for example, to include a quantizer 33 and computer 34 for quantizing the signal $E_O$ to obtain digital data representing the body transmissivity along various straight line paths through the body and for processing such data for presentation to a graphic display terminal 36 to compose a picture or other graphic display.

The quantizer 33 is a high speed analog-to-digital converter which repetitively samples the signal $E_O$ and converts each sampled value to a digital representation. This information is then supplied to the memory of the computer 34. As the sampling takes place, information is also available in the computer, commanded through line 19, identifying the position of the beam during each sampling period. Such beam position information is also provided to the computer memory or storage means, and it is stored as a scanned raster of beam position and transmissivity. This stored information is then processed by the computer in accordance with the desires and dictates of the user to compose a graphic display at the graphic display terminal 36 revealing the details of internal body features. The computer memory may, of course, be a magnetic tape, a magnetic drum or other record device for permanent storage of the information. Also, it will be understood that the computer may utilize various different programs, either automatically or under user command, executing algorithms for enhancing, eliminating or clarifying image features. Also because of the great amount of information made available by the great dynamic range of the system, the computer may be used to produce from a single exposure a number of different pictures or other graphic displays corresponding to those presently obtained by taking photographs during successive exposures of different levels of X-ray intensity. A very useful form of graphic display device is a cathode ray tube which immediately displays images created by image signals supplied by the computer and which image signals may be modified by the users' requests, concerning enhancement, elimination of features, etc. inputed to the computer. When a desirable image is obtained, a permanent photograph of the display screen may then be made for further analysis.

Figure 2:
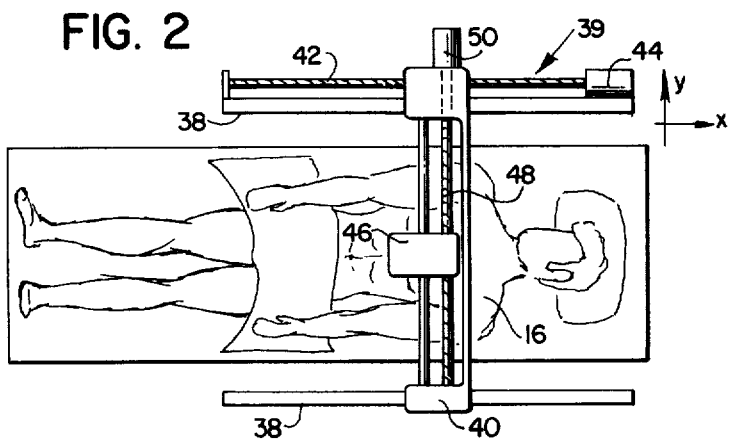
FIG. 2 is a top view of an X-ray generator, collimator, and scanning device which may be used in the system of FIG. 1.

The construction and particular kind of components used to make up the X-ray generator, the collimator and scanner of the mechanism 10 of FIG. 1 may vary widely without departing from the invention. By way of example, however, FIGS. 2, 3 and 4 show one form such structure may take. Referring to these figures the mechanism 10 includes a scanner in the form of an X-Y coordinate positioning mechanism 39 generally similar to that commonly found in X-Y plotters and drafting machines. In particular, and referring to FIG. 2, the mechanism 39 includes two parallel rails or guides 38, 38 which support a main carriage 40 for movement in the illustrated X coordinate direction. The carriage 40 is in turn driven and positioned in the X coordinate direction by a lead screw 42 driven by a motor 44. Supported on the main carriage 40 is a smaller work carriage 46 which is movable relative to the carriage 40 in the illustrated Y coordinate direction, such movement being effected by another lead screw 48 and associated drive motor 50.

As shown in FIG. 4, the work carriage 40 supports an X-ray tube 52 enclosed by a housing 54 of suitable radiation shielding material. This housing includes an elongated nozzle 56 with a straight bore 58. The tube 52 is designed and positioned so that the X-rays generated thereby are directed generally toward the bore 58, and the nozzle 56 is of sufficient length that the rays exiting therefrom are contained in a relatively well collimated beam 12.

The detector 14 as shown in FIGS. 3 and 4 is a unit having a relatively small sensing area and is moved in unison with the beam 12 so as to be at all times directly in line with it. For this purpose, the detector shown in FIG. 3 is mounted on the work carriage 60 of an X-Y positioning mechanism 61 similar to the mechanism 39 used for moving the beam generator. The movement of the beam 12 in its scanning motion is controlled by the scanning motion control unit 17 and the computer of FIG. 1 which supplies positioning drive signals to the drive motors 44 and 50 of the mechanism 39. The same signals are also supplied to the corresponding motors of the detector positioning mechanism 61 to cause the two positioning mechanisms to operate in unison.

FIG. 5 shows a typical scanning path for the beam 12. In this figure, the lines 62, 62 represent lines along which the beam 12 is successively moved by the scanner. These lines are spaced from one another by a distance substantially equal to the beam diameter, and as the beam is moved along each line 62 the value of the output signal $E_O$ is repetitively sampled by the quantizer 33, the time between each sample being approximately equal to the time required for the beam to move one beam diameter along the line 62. Thus, the information derived during the scanning movement of the beam describes the transmissivity of the body at all points of a position matrix, and from it a graphic display may be composed.

It should especially be understood, however, that the invention is not necessarily limited to the above described type of scanning motion and that it may be used with various different types of scanning procedures. For example, U.S. Pat. No. 3,778,614 describes an apparatus for producing a graphic display from information derived from a plurality of scans taken at different angles around a body or body part, and the system of this invention may be adapted and used to perform such type of scans.

An important feature of this invention is that the scanning system is a closed loop control system whereby an extremely large dynamic range in the output signal is made possible. This will be evident from FIG. 6 wherein the components of FIG. 1 have been arranged to show more clearly the closed loop nature of the system. From this figure it will be seen that the feedback circuit for the amplifier 28 consists of the X-ray tube or generator 52, its related intensity control 30, the body 16 under examination and the detector 14. The generator 52 and the detector 14 are coupled by the beam 12 which passes through the body and which has its intensity modified in accordance with the transmissivity of that portion of the body through which it passes. The entire feedback circuit is indicated at 64 and has a feedback coefficient B providing a feedback voltage $BE_O$ to the summing circuit 26. The feedback factor B is significant, and the gain of the amplifier 28 is very large, so that $|AB|$ is very much greater than one. With this being the case, it will be understood that the system operates to hold the feedback voltage essentially equal to the reference voltage. Therefore $E_O = E_R/B$. That is, $E_O$ is inversely proportional to the feedback coefficient B. The feedback coefficient B in turn is a function solely of the transmissivity of the body 16 since it is the only variable in the feedback circuit 64, the characteristics of the X-ray generator 52, the intensity control 30, and the detector 14 being fixed.

The feedback coefficient B of the systems of FIG. 6 may be a nonlinear function of the transmissivity of the beam path, and therefore the output signal $E_O$ is also a nonlinear function of the transmissivity. In some cases it may be desirable to remove this nonlinearity, or to reshape it, and this may be accomplished by adding to the feedback circuit 64a, as shown in FIG. 7, an amplifier, network or other component 66 having a transfer function intentionally designed to compensate for the nonlinearity and to cause the feedback coefficient to be a linear, logarithmic or other desired function of the transmissivity.

Figure 8:
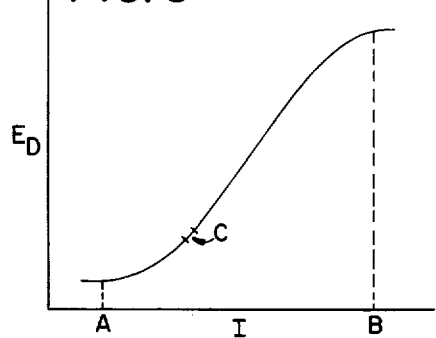
FIG. 8 is a graph showing a typical response curve for an X-ray detector such as used in the system of FIG. 1.

FIG. 8 shows the general nature of a response curve for a radiation detector, such as the detector 14, which may be used in the system of this invention, and by reference to the figure, a further understanding of the increased dynamic range of the output signal provided by the system of this invention may be had. The horizontal axis represents the intensity I of the beam striking the detector and the vertical axis represents the corresponding output voltage $E_D$. In a prior art system wherein a body is exposed to a constant intensity beam or field of radiation the detector is capable of detecting only those X-ray absorbtion or transmissivity values causing the detected intensity to fall between the minimum value A and the maximum valve B of FIG. 8. For instance, if one body part is exposed to a given intensity of radiation and has an X-ray absorption factor of one which produces a maximum detected intensity B and if another body portion having an absorption factor fifty when exposed to the same intensity of radiation causes a minimum detected intensity A, the range of the system is from an absorption factor of one of an absorption factor of fifty. Absorption factors falling outside of this range cannot be distinguished from one another. Further, the curve of FIG. 8 is nonlinear at both its lower and upper ends making intensity detections relatively inaccurate in the region of these end portions.

In the system of this invention, however, only a very small portion of the response curve of FIG. 8 is utilized. That is, the system operates to maintain the detected intensity relatively constant and indeed the detected intensity varies by only small amounts. For example, the system, may operate with detected intensity changes, occurring only within the very small region C of the curve of FIG. 8, and the system is preferably so designed that this region is located within the linear portion of the curve and also at the lower end of such linear portion so as to maintain as low as possible the associated level of the body-incident beam intensity. Since only a small portion of the response curve is used, the limited range of the detector does not limit the range of the system. If the beam passes through a body portion having an absorption factor of one, the beam intensity is controlled to cause the detected intensity to remain within the small region C of FIG. 8. Likewise, if the beam passes through a body part having an absorption factor of one thousand, the beam intensity is again adjusted to maintain a detected intensity within the region C of FIG. 8. Accordingly, the dynamic range of the system of the invention is limited only by the limits between which the intensity of the body-incident beam may be varied, and this range of possible beam intensities is very great.

In practicing this invention, various different means may be used to dynamically vary the intensity of the emitted or body-incident beam of radiation and to provide the beam control signal which is used as a source of information about the radiation transmissivity or absorption of the body part through which the beam instantaneously passes. Several different such means are shown in FIGS. 9, 10, 11 and 12.

Figure 9:
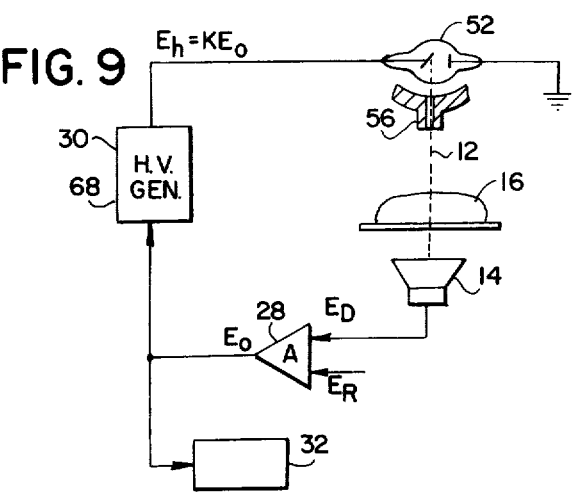
FIG. 9 is another diagrammatic view of the system of FIG. 1 showing more specifically the means for varying the body-incident beam intensity.

Referring first to FIG. 9, in the system there illustrated, the intensity of the emitted or body-incident portion 18 of the beam 12 is varied by varying the anode-to-cathode voltage of the X-ray tube 52. The beam intensity control 30 in this case is a variable high voltage generator 68 which responds to the output or control voltage $E_O$ to provide a high voltage $E_h$ supplied to the anode of the tube 52. $E_H$ is a function of $E_O$, preferably a linear function so that $E_h = KE_O$ where $K$ is a constant. It is further well-known that varying the anode-to-cathode voltage of an X-ray tube not only varies the intensity of the emitted beam but also varies its mean wavelength, the mean wavelength decreasing as the anode-to-cathode voltage, and beam intensity, is increased. Thus, as the emitted beam intensity is increased, as a result of it encountering more dense material, it is simultaneously hardened to give it an increased penetrating ability. This fact may be taken advantage of in some situations to enable the bringing out of even more detail in the resulting graphic display.

Figure 10:
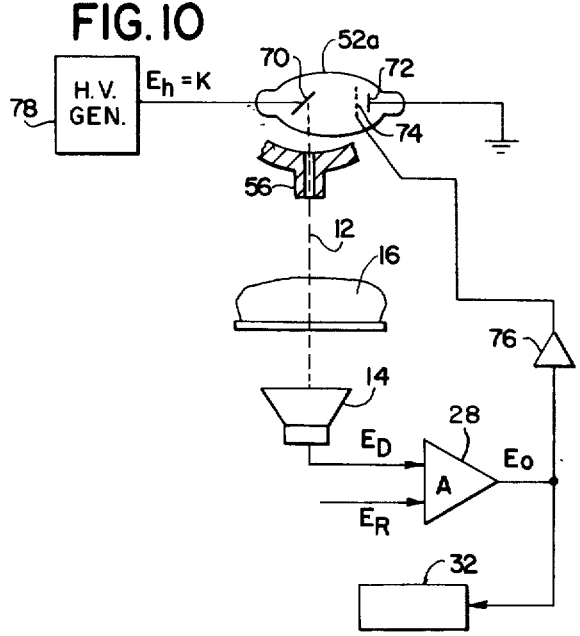
FIG. 10 is a diagrammatic view similar to FIG. 9 but showing an alternate embodiment of the invention.

In the system of FIG. 10 the intensity of the emitted or body-incident portion 18 of the beam is varied by utilizing an X-ray tube 52a including, in addition to an anode 70 and a cathode 72 a control grid 74. The voltage applied to the control grid 74 is in turn varied in accordance with variations in the output voltage $E_O$ through an amplifier 76. The anode-to-cathode voltage is maintained at a fixed value by an associated high voltage generator 78. Therefore, during the operation of the system the mean wavelength of the emitted beam remains fixed, due to the fixed anode-to-cathode voltage, and only the intensity of the emitted beam is varied through the agency of the control grid 74.

Figure 11:
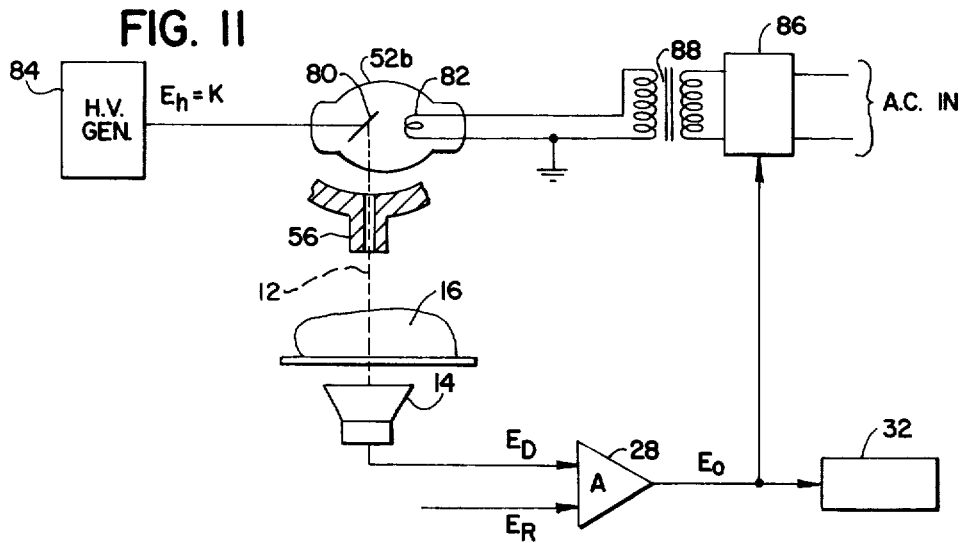
FIG. 11 is a diagrammatic view similar to FIG. 9 but showing still another embodiment of the invention.

FIG. 11 shows another embodiment of the invention wherein only the intensity and not the wavelength of the emitted or body-incident beam is varied. Referring to this figure, the illustrated system utilizes an X-ray tube 52b with an anode 80 and a heated electron emitting element 82. The element 82 is a filament which in the illustrated case also serves as the cathode. A fixed high voltage is applied across the anode 80 and the cathode-filament element 82 by a high voltage generator 84. The electron beam current flowing between the anode 80 and the element 82, and accordingly the intensity of the emitted beam, is controlled by varying the heating current supplied to the element 82. This control of the heating current may be effected in various different ways, and the illustrated case accomplished by means of a control amplifier 86 and a transformer 88. In response to changes in the output signal $E_O$ the control amplifier 86 varies the current supplied to the primary of the transformer 88 and the resulting current induced in the secondary for energizing the element 82. The element 82 is preferably one having a fast thermal response time to allow a fast response for the entire system, and for the same reason the frequency of the input power supplied to the control amplifier 86 is also preferably relatively high.

In all of the systems shown in FIGS. 9, 10, and 11, the output signal from the amplifier 28 is used as the beam control signal which is also supplied to the utilization device for the extraction of transmissivity information.

Figure 12:
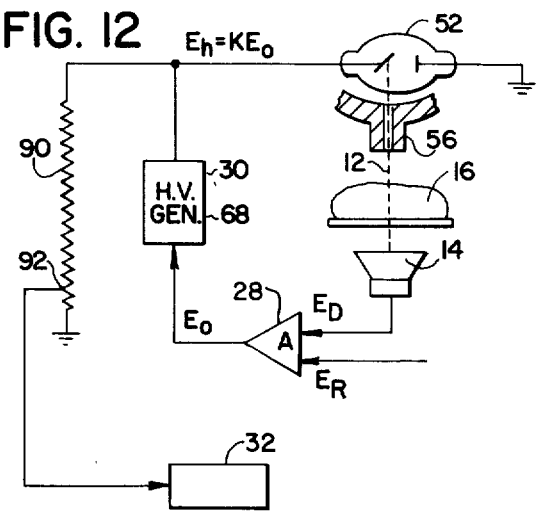
FIG. 12 is a diagrammatic view similar to FIG. 9 but showing another embodiment of the invention.

FIG. 12, on the other hand, shows a system wherein the beam intensity is varied by varying the anode-to-cathode voltage of an X-ray tube 52, as in FIG. 9, but wherein the output signal to the utilization device is taken from the output side of the high voltage generator. In particular, the output circuit includes a voltage divider 90 connected in parallel with the tube 52 having a voltage tap 92 from which a very small portion of the voltage appearing across the voltage divider is extracted and used as the signal supplied to the utilization device 32.

I claim :

1. A system for examining a body by a beam of penetrating radiation, said system comprising:
    means for providing a collimated beam of penetrating radiation and for moving said beam relative to a body to be examined to cause it to have a succession of different straight line paths passing through said body,
    a detector for detecting the intensity of said beam after passage through said body and for producing a corresponding detected intensity signal,
    means responsive to said detected intensity signal for varying the emitted intensity of said beam to maintain said detected intensity signal at an essentially constant value,
    means for providing an output signal having a value corresponding to the value of said emitted intensity of said beam, and
    means utilizing said output signal as a source of information about the transmissivity of said body along each of said different straight line paths.

2. A system as defined in claim 1 further characterized by said means utilizing said output signal being means for generating from said output signal a graphic display of internal features of said body.

3. A system as defined in claim 1 further characterized by said means utilizing said output signal being an analog to digital quantizer for quantizing said output signal into digital data, a graphic display terminal, and a computer for processing said digital data to create therefrom a graphic output from said graphic display terminal.

4. A system for examining a body by a beam of penetrating radiation scanned thereover, said system comprising:
    a ray generator and scanner for producing a beam of penetrating radiation and for moving said beam in a scanning manner relative to a body to be examined,
    said ray generator and scanner including a means for varying the intensity of said beam of penetrating radiation in response to variations in a related control signal,
    a detector for detecting the intensity of that portion of said beam which is transmitted through and exits from said body and for producing a corresponding body-exiting radiation intensity signal,
    means for continuously comparing said body-exiting radiation signal with a reference signal and for continuously varying said control signal in such manner as to maintain said body-exiting radiation signal instantaneously equal to said reference signal, and
    means utilizing said control signal repetitively during the scanning movement of said beam as a source of information about the transmissivity of said body along the instantaneous path of said beam.

5. A system as defined in claim 4 further characterized by said means utilizing said control signal being means for generating from said control signal a graphic display of internal features of said body.

6. A system as defined in claim 4 further characterized by said ray generator being an X-ray tube having an anode and a cathode, and said means for varying the intensity of said beam being a variable high voltage generator for applying a high voltage across said anode and cathode and varying said high voltage in response to said control signal.

7. A system as defined in claim 4 further characterized by said ray generator being an X-ray tube having an anode, a cathode and a grid, means for applying a fixed high voltage across said anode and cathode, and said means for varying the intensity of said beam being means for applying a voltage to said grid which varies in accordance with variations in said control signal.

8. A system as defined in claim 4 further characterized by said ray generator being an X-ray tube having an electron emitting element heated by a heating current, and said means for varying said intensity of said beam being means for varying said heating current in response to variations in said control signal.

9. A scanning type penetrating ray system for examining a body, said system comprising;
    a voltage amplifier having an output voltage $E_O$,
    means for providing a reference voltage $E_R$,
    a feedback circuit connected to the output of said amplifier and having a feedback coefficient B so as to provide a feedback voltage $BE_O$,
    means for summing said reference voltage $E_R$ and said feedback voltage $BE_O$ to obtain a resultant error voltage $e = E_R + BE_O$ and to supply said error voltage $e$ to said amplifier as the input thereto,
    said feedback circuit comprising a penetrating ray generator for producing a beam of penetrating rays having an emitted intensity which is a function of said output voltage $E_O$, a detector in the path of said beam of ray operable to produce an output voltage which is a function of the intensity of the rays impingent thereon, and an examining space between said ray generator and said detector into which a body to be examined may be placed so as to be in the path of said beam,
    scanning means for moving said beam in a scanning fashion so that its path successively passes through different portions of a body placed in said examining space,
    and means utilizing said output voltage $E_O$ as a source of information about the transmissivities of those portions of said body through which said beam path is successively moved by scanning means.

10. A scanning type penetrating ray system as defined in claim 9, further characterized by said amplifier having a gain A and said gain feedback coefficient B being of such relative values that $|AB|$ is very much greater than one.

11. A scanning type penetrating ray system as defined in claim 9 further characterized by said feedback circuit further including a component having an intentionally designed transfer function for causing said feedback coefficient B to have a desired functional relationship to the transmissivity of the path of said beam through said body.

12. A system for examining a body by a beam of penetrating radiation, said system comprising:

means for providing a collimated beam of penetrating radiation and for moving said beam relative to a body to be examined to cause it to have a succession of different straight line paths passing through said body, a detector for detecting the intensity of said beam after passage through said body and for producing a corresponding detected intensity signal, means responsive to a control signal for varying the emitted intensity of said beam and for simultaneously varying the mean wavelength of said beam in such a manner that said mean wavelength is decreased as said emitted beam intensity is increased, means response to said detected intensity signal for varying said control signal so as to maintain said detected intensity signal at an essentially constant value, and means utilizing said control signal as a source of information about the transmissivity of said body along each of said different straight line paths.

13. A system as defined in claim 12 further characterized by said means for providing a collimated beam of penetrating radiation comprising an X-ray tube having an anode and a cathode, and said means for simultaneously varying said emitted intensity and said mean wavelength of said beam comprising a variable high voltage generator for applying a high voltage across said anode and cathode and for varying said high voltage in accordance with variations in said control signal.

14. A method for examining a body through the use of a beam of penetrating radiation, said method comprising the steps of:

scanning a beam of penetrating radiation over a body to be examined, dynamically varying the body-incident intensity of said beam to maintain at a constant value its body-exiting intensity, dynamically providing a measurement of said body-incident intensity of said beam, and utilizing the instantaneous value of said body-incident beam intensity measurement as an indication of the transmissivity of that portion of said body through which said beam instantaneously passes.

15. A method for examining a body through the use of a beam penetrating radiation, said method comprising the steps of:

scanning a beam of penetrating over a body to be examined, dynamically varying a control signal, which in turn varies the body-incident intensity of said beam, to maintain at a constant value the body-emitting intensity of said beam, and utilizing the instantaneous value of said control signal as an indication of the transmissivity of that portion of said body through which said beam instantaneously passes.

16. The method of examining a body though the use of a beam of penetrating radiation, said method comprising the steps of:

scanning a beam of penetrating radiation over a body to be examined, dynamically varying a control signal, which in turn varies the body-incident intensity of said beam, to maintain at a constant value the body-exiting intensity of said beam, repetitively sampling the value of said control signal during said scanning of said beam, and, utilizing said repetitively sampled values of said control signal as representations of the transmissivities of those portions of said body through which said beam passes during the corresponding sampling periods.

17. A method of examining a body through the use of a beam of penetrating radiation as defined in claim 16 further characterized by:

said step of utilizing said sampled values of said control signal being that of generating from said sampled values a graphic display of internal features of said body, 18. The method of examining a body through the use of a beam of penetrating radiation, said method comprising the steps of:

scanning a beam of penetrating radiation over a body to be examined, providing a control for said beam which control in response to a control signal varies the emitted intensity of said beam, dynamically varying said control signal to in turn vary said emitted intensity to maintain the body-exiting intensity of said beam at a constant value, repetitively sampling the value of said control signal during said scanning of said beam, and utilizing said repetitively sampled values of said control signal as representations of the tranmissivities of those portions of said body through which said beam passes during the corresponding sampling periods.

19. The method of examining a body through the use of a beam of penetrating radiation, said method comprising the steps of:

scanning a beam of penetrating radiation over a body to be examined, providing a control for said beam which control in response to a control signal simultaneously varies both the emitted intensity and the mean wavelength of said beam, dynamically varying said control signal to in turn simultaneously vary both said emitted intensity and said mean wavelength of said beam to maintain the body-exiting intensity of said beam at a constant value, repetitively sampling the value of said control signal during said scanning of said beam, and utilizing said repetitively sampled values of said control signal as representations of the transmissivities of those portions of said body through which said beam passes during the corresponding sampling periods.

* * * * *